United States Patent [19]

Orelup

[11] 4,209,302
[45] Jun. 24, 1980

[54] MARKER FOR PETROLEUM FUELS
[75] Inventor: Richard B. Orelup, Upper Saddle River, N.J.
[73] Assignee: Morton-Norwich Products, Inc., Chicago, Ill.
[21] Appl. No.: 37,875
[22] Filed: May 10, 1979
[51] Int. Cl.² ............................................ C10L 1/22
[52] U.S. Cl. .................................... 44/59; 44/63; 544/165; 260/570.5 P
[58] Field of Search ............... 44/59, 63; 260/570.5 P; 544/165

[56] References Cited
U.S. PATENT DOCUMENTS

| | | | |
|---|---|---|---|
| 2,670,376 | 2/1954 | Scudi et al. | 260/570.5 P |
| 3,658,781 | 4/1972 | Hegar | 544/165 |
| 4,080,380 | 3/1978 | Zenitz | 260/570.5 P |

Primary Examiner—Patrick Garvin
Assistant Examiner—Y. Harris-Smith
Attorney, Agent, or Firm—Jack Axelrood

[57] ABSTRACT

New markers for petroleum fuels; a method of marking said fuels with a marker and of subsequently detecting the presence of said marker; and marked fuels are provided. The markers include the following compounds:

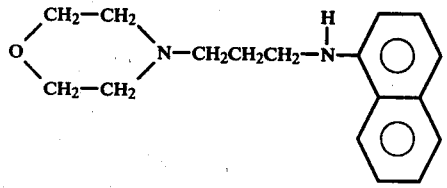

(I)

1-(4-morpholino)-3-(alpha naphthylamino)-propane,

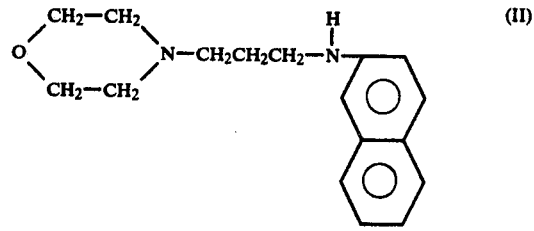 (II)

1-(4-morpholino)-3-(beta naphthylamino)-propane,

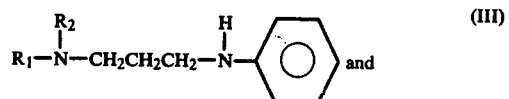 (III)

and

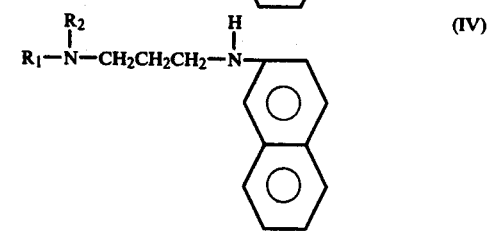 (IV)

where $R_1$ and $R_2$ may be hydrogen or alkyl having from one to twenty carbon atoms.

The marker is detected in said marked fuel by (1) extraction with an acidic aqueous solution and (2) admixture with a stabilized solution of diazotized 2-chlor-4-nitroaniline to yield a color characteristic of the marker.

31 Claims, No Drawings

MARKER FOR PETROLEUM FUELS

BACKGROUND OF THE INVENTION

1. Field of the Invention

There is a need for novel markers which are particularly suitable for marking water immiscible organic liquids such as petroleum fuels and which markers may be extracted easily from said marked liquids and identified. There is also a need for marked fuels and for means to mark, tag or otherwise identify petroleum fuels or other organic solvents, and to distinguish such marked liquids from the otherwise identical but unmarked substances.

These needs arise primarily from differing price or tax structures of different fuels or even the same fuel used for different purposes. For example, gasoline used for off-highway, non-vehicular purposes such as mining, lumbering or fishing, is commonly taxed at lower rates than that for highway vehicular use. Further, certain grades of oil are used interchangeably for heating oil or for diesel motor fuel. These situations can lead to abuse of the tax laws and cheating by unscrupulous persons.

It is, of course, necessary that the added chemical marker be capable of quick and relatively simple identification by non-scientific personnel. In other instances and aside from tax matters, there are occasions when it is desirable to mark a particular production batch of fuel or solvent to prove the origin of the material. As is readily apparent, any marker so used must be added in small concentration, should not affect the physical or chemical properties of the substances to which it is added and should be easily identified by relatively quick and simple means.

It is desirable to have simple, rapid and sensitive methods to detect the presence of one petroleum product in another. Fuels are sometimes mixed for the purpose of adulterating a higher priced product with a lower priced material, such as the addition of regular grade gasoline to premium gasoline, or for the purpose of evading taxation by the addition of low-taxed light heating oil to highly taxed diesel fuel. Other reasons for identifying particular fuels are determination of theft, or locating leaks from storage facilities at service stations, oil terminals, large scale industrial lubrication systems, or automotive transmission and hydraulic systems.

2. Description of the Prior Art

Among the many additives and tracers which have been proposed for use or are in current use for marking or tagging motive fuels and other petroleum distillates are the metal-organic compounds, radioactive substances, and a variety of specific compounds which react with selected agents to provide intensely colored derivatives. However, many of the proposed additives and those in use have certain disadvantages which render them impractical for marking purposes. For example, the metal-organic compounds have relatively poor storage stability. The use of radioactive substances requires special equipment and precautionary measures to prevent harmful physiological disturbances to personnel. With respect to the specific compounds which have been employed for marking purposes, there may be mentioned quinizarin, furfural, diphenylamine, and various naphthol derivatives.

Quinizarin, though an excellent marker which is extracted from petroleum fuels by aqueous caustic solutions, suffers from the disadvantage of low solvent solubility, i.e., its solubility is generally of the order of magnitude of about 1 percent or less in the commonly used solvents. The relative insolubility of quinizarin in fuel-compatible solvents means that it must be transported and used in dry state with the attendant handling problems due to dusting and low solubility, and precludes the possibility of providing a solution containing as much as about 20 or 40% quinizarin. The use of a relatively dilute quinizarin solution would require the handling, storage and metering of large volumes, a situation which is undesirable both from a handling and economic point of view.

Furfural develops an intense red-colored complex with aniline acetate. However, the furfural test is extremely sensitive and the smallest contamination by any furfural naturally present in the liquid to be marked yields a distinct red color. Since a small quantity of furfural is sometimes produced in the normal production of middle petroleum distillates, a positive furfural test is not necessarily conclusive evidence of the presence of added furfural. The same is true of diphenyl amine and various naphthols which may originate in crude oil or arise from the cracking or refining process. Further, at the concentrations generally used in fuels, furfural is unstable to the extent that no positive identification will be obtained after a normal storage period of up to six months. Other specific marking agents, for example, aniline azo beta naphthol, are extracted from fuels to which they are added by the extractants dimethylformamide or benzyl alcohol to yield a yellow colored extract. However, some times a yellow extract can be obtained from unmarked petroleum fuels, thereby vitiating the test. Oil soluble dyes such as Solvent Red #24 and Solvent Red #19 have also been used for marking fuels, with identification dependent upon dye recognition.

Accordingly, it would be desirable and is an object of this invention to provide novel markers for petroleum fuels, which markers have the following characteristics:

1. Entirely foreign to the fuel.
2. Can be supplied as liquids having high solubilities in petroleum fuels.
3. Colorless.
4. Do not alter the appearance of the fuel to which added.
5. Easily extracted from the marked fuel.
6. When extracted from the marked fuel, they are easily identified by a simple, on-the-spot test which is not subject to interference by the components of the fuel.
7. The identification can be corroborated by laboratory methods, if necessary.

The fulfillment of these desiderata and objects of this invention may be more readily appreciated by reference to the following specification, examples and appended claims.

SUMMARY OF THE INVENTION

This invention provides markers for petroleum fuels, said markers being selected from the group consisting of the following:

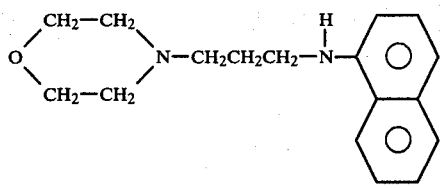

1-(4-morpholino)-3-(alpha naphthylamino)-propane,

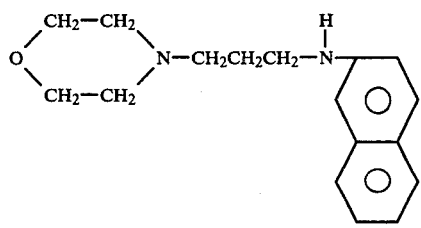

1-(4-morpholino)-3-(beta naphthylamino)-propane,

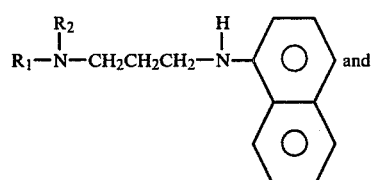 and

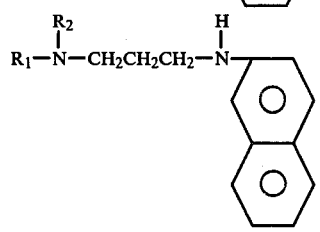

where $R_1$ and $R_2$ may each be hydrogen or alkyl having from one to twenty carbon atoms.

The marker is added to a petroleum fuel in a concentration as low as about one half to one part per million of fuel, in which it dissolves without imparting any color to the fuel or otherwise indicating its presence to the naked eye. Thereafter, the marked fuel is extracted with a relatively small portion of an aqueous acidic solution which removes and concentrates the marker in the aqueous phase. The aqueous phase containing the marker is separated from the fuel and treated with a small quantity of a stabilized solution of diazotized 2-chlor-4-nitroaniline whereupon a characteristic pink coloration develops instantly. This procedure of marker extraction and treatment with stabilized diazotized 2-chlor-4-nitroaniline is hereinafter referred to as the "detection procedure". A control, unmarked fuel carried through the same detection procedure, either does not develop any color, or assumes a pale yellow to brownish hue, depending upon the nature and components of the original fuel.

The marker is usually added to the fuel at a concentration of about 12 parts per million, at which concentration it imparts no coloration to the fuel. At 12 parts per million, the marker gives an intense bluish-pink coloration when carried through the described detection procedure. At this level, if the marked fuel is admixed with an unmarked fuel in a concentration as little as 4 parts of marked fuel per 96 parts of unmarked fuel, the resulting concentration of marker in the mixture will be 0.5 part per million, a concentration which is easily detected by the described detection procedure.

The presence of the marker by the aforedescribed detection procedure may be confirmed by extracting the aqueous acidic extract with an immiscible polar solvent, such as amyl alcohol or hexyl cellosolve, which extracts the marker and changes its shade to purple. This polar solvent solution of the marker also may be spotted on silica gel-coated plates for thin layer chromatography. These techniques serve to distinguish the marker from any natural fuel component colors which may mask the marker color at very low concentrations. The term "petroleum fuel" or "fuel" as used herein, means such petroleum-derived products as gasolines, diesel oils, heating or fuel oils, kerosenes, jet fuels, naphthas and the like.

The aqueous acidic solution which is used to extract the marker from the marked fuel may be a solution of methane sulfonic acid or hydrochloric acid. A convenient methane sulfonic acid solution is one containing 2% by weight of methane sulfonic acid. A 2% or 3% solution of hydrochloric acid in water may also be used. The specific acid used in the aqueous acidic solution may be varied as desired or needed in accordance with the nature of the fuel under consideration.

An important element in the detection of the marker is the diazotized 2-chlor-4-nitroaniline solution. Normally, diazotized aromatic amines are relatively unstable, and when used for preparation of azo dyes, are reacted in the azo coupling as soon as possible after diazotization is complete. This is carried out in a period of a few minutes up to a few hours to avoid decomposition of the diazo compound, often accompanied by evolution of nitrogen and formation of resinous materials. During diazotization and coupling, it also is usual practice to keep diazo compounds at low temperatures, frequently around 0° C., and to avoid light, in order to further repress decomposition.

It has been found that when 2-chlor-4-nitroaniline is diazotized in a non-aqueous medium, particularly glacial acetic acid, the resulting pale yellow diazo solution is very stable. For example, a standardized solution has been observed to retain more than 75% of its initial activity when stored for six months at temperatures of 18° C. to 35° C., in a brown bottle, and to be still highly active after one year. Since testing of marked fuel samples desirably are to be performed by enforcement officers in the field, rather than under laboratory conditions, an effective diazo reagent must be stable for lengthy periods of time under ambient temperature conditions.

The markers described above (I–IV) have moderate fuel solubilities per se. For convenience in handling, storage and metering into fuels, these markers may be converted to a permanent liquid state, soluble in all proportions in petroleum fuels and colorless at use concentrations, by admixture with fatty acids and solvents. For example, a typical formulation involving marker (I) would be the following:

Marker I 34%
Oleic Acid 39%
Xylene 27%

The specific fatty acids and solvents, and their proportions, may be varied as desired to provide the liquid, highly soluble markers for commercial use.

The present invention also provides a method of marking a fuel and detecting the presence of said marker in the fuel, which method comprises adding to the fuel a marker (I–IV) as described in a concentration which may be as low as one half to one part per million of fuel. Generally, about 35 parts per million of the marker formulation is added to the fuel so that it gives an intense characteristic color reaction when subjected to the detection procedure, and which, even if diluted as much as 20 to 25 times with an unmarked fuel or organic solvent will still show the presence of marker by the same detection procedure. The present invention also provides marked fuels characterized in that they contain at least about one half to one part per million of a marker (I–IV) as defined, and which marked fuels show no visible evidence of having been marked, and which marked fuels can be carried through the detection procedure to confirm the presence of one of said markers.

For a more complete understanding of the present invention, reference is now made to the following specific examples illustrating the novel makers, marking process, marked fuels and identification procedure of the present invention.

DESCRIPTION OF THE PREFERRED EMBODIMENTS

EXAMPLE 1

Preparation of 1-(4-morpholino)-3-(alpha naphthylamino)-propane.

In a flask fitted with a stirrer, thermometer, reflux condenser and water trap, 144 grams of alpha naphthol and 172.8 grams (4-(3-aminopropyl)-morpholine are heated together at reflux with 4 grams of iodine (catalyst) and 20 ml. of xylene.

Over a period of several hours at 210°–225° C., 30–35 milliliters of a mixture of water and 4-(3-aminopropyl)-morpholine are collected in the water trap. When evolution of the watery phase becomes very slow, the reaction is cooled below 100° C., and the oily product is washed with 400 ml portions of 10% sodium hydroxide at 90° C. until neutralized samples of the washings give no further precipitation. The oil phase then is washed once with hot water and the pH adjusted to 7 with a small amount of acid, before final separation.

The product is freed from water and volatile matter by stripping distillation, yielding about 180 grams of crude 1-(4-morpholino)-3(alpha naphthlamino) propane. The marker may be isolated as is, or immediately mixed with 205.2 grams of oleic acid and 146.5 grams of xylene. After filtration from a small amount of salts, a uniform, stable, oil liquid composition remains.

EXAMPLE 2

Marker Detection

Twelve grams of the marker of Example #1 are dissolved in one cubic meter of regular grade gasoline, producing a concentration of 12 parts per million (weight/volume), and imparting no color to the gasoline.

Forty milliliters of the so marked regular gasoline are shaken together with four milliliters of a 2% solution of methane sulfonic acid in water, in a small separatory funnel, then allowed to stand while the water phase separates quickly to the bottom, from where it is removed.

Five drops of 0.02 molar diazotized 2-chloro-4-nitroaniline in acetic acid solution are added to the colorless water extract. An intense bluish pink color develops within a few seconds.

It is understood that none of the preceding quantities are critical and are given only for the purpose of illustration.

EXAMPLE 3

Forty milliliters of unmarked premium gasoline are extracted according to the procedure of Example #2. No color develops immediately on addition of the diazotized 2-chloro-4-nitro-aniline to the acidic aqueous extract. A weak yellow color appears after several seconds and slowly intensifies.

EXAMPLE 4

Four cubic meters of the marked regular grade gasoline of Example #2 are mixed with 96 cubic meters of premium gasoline to produce 100 cubic meters of mixed gasolines containing 0.5 ppm of marker. Fifty milliliters of the mixed gasolines are shaken together with four milliliters of 3% aqueous hydrochloric acid in a small separatory funnel, then allowed to stand while the water phase separates to the bottom and is removed.

Three drops of 0.02 molar diazotized 2-chlor-4-nitroaniline in acetic acid solution are added to the colorless watery extract.

A pink color develops within a few seconds, indicative of the presence of the marker.

EXAMPLE 5

Twelve grams of the marker of Example #1 are added to one cubic meter of #2 heating oil producing a concentration of 12 parts per million (weight/volume).

Forty milliliters of the marked #2 heating oil are treated according to the procedure of Example #2. An intense bluish pink positive marked fuel test is obtained.

EXAMPLE 6

Five cubic meters of the marked #2 heating oil of Example #5 are mixed with 95 cubic meters of #2 diesel fuel to produce a mixture of fuel oils containing 0.6 ppm of marker. Fifty milliliters of the mixture are tested according to the procedure of Example #2.

A red coloration is obtained, indicative of the presence of the marker. The finished red extract is further shaken with one milliliter of n-amyl alcohol and a few drops of ammonium hydroxide. All color migrates to the floating alcohol layer, which becomes reddish purple in the absence of fuel impurities.

Five microliters of the alcohol extract are spotted near the base of a standard silica gel coated thin layer choromatographic glass plate.

The chromatogram is developed with a mixture of 90 parts ethyl alcohol and 10 parts water. The marked fuel color is observed to rise from the origin as a purple spot, while the yellow brown color of any fuel impurities moves clearly ahead of the marker.

EXAMPLE 7

Two hundred and seventy six grams of a mixture of propane diamines commercially available under the trademark "Duomeen C", prepared from the reaction of dodecyl amines with acrylonitrile and subsequent reduction to form a mixture of substituted propane diamines, is heated together with 172.8 grams of beta naphthol, 3 grams of iodine (catalyst) and 20 ml. of xylene in a reactor fitted with stirrer, thermometer, reflux condenser and water trap.

The mass is refluxed at 210°–225° C. while water is produced and collected. When the reaction is essentially complete, as evidenced by almost no further water evolution, it is cooled and washed with portions of hot dilute aqueous potassium hydroxide. When excess beta naphthol has been removed the product is neutralized, and freed of water and solvent by stripping distillation to provide a marker operable in the present invention.

The finished product (marker) is moderately soluble in petroleum fuels and exhibits the same positive marked fuel test when added to gasoline oil and carried through the identification procedure described in Example 2.

If desired, this marker may be converted to a highly soluble liquid form by admixture with ethylhexanoic acid and xylene.

I claim:

1. A marker for petroleum fuels, said marker being selected from the group consisting of:

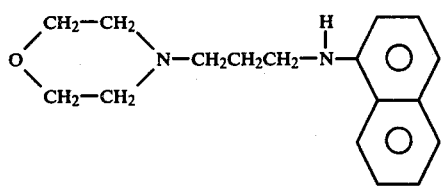

(I)

1-(4-morpholino)-3-(alpha naphthaylamino)-propane,

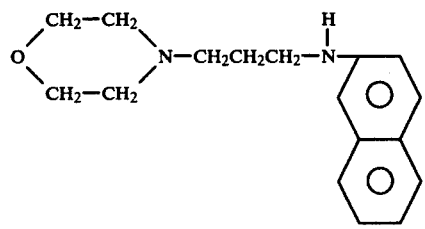

(II)

1-(4-morpholino)-3-(beta naphthylamino)-propane,

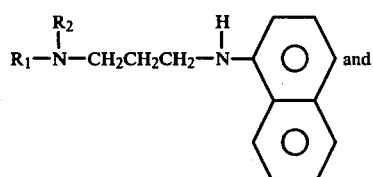

(III)

and

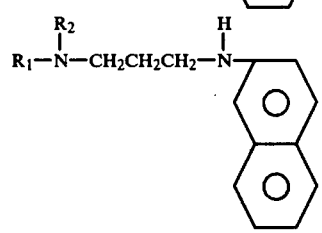

(IV)

where $R_1$ and $R_2$ may each be hydrogen or alkyl having from one to twenty carbon atoms.

2. The marker for petroleum fuels of claim 1 wherein the marker is the compound

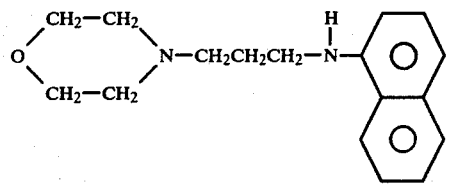

1-(4-morpholino)-3-(alpha naphthylamino)-propane.

3. The marker for petroleum fuels of claim 1 wherein the marker is the compound

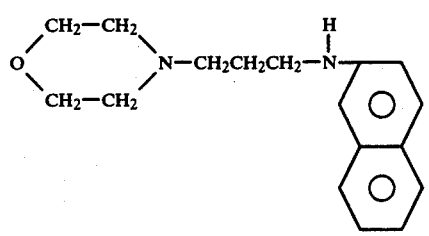

1-(4-morpholino)-3-(beta naphthylamino)-propane.

4. The marker for petroleum fuels of claim 1 wherein the marker is the compound

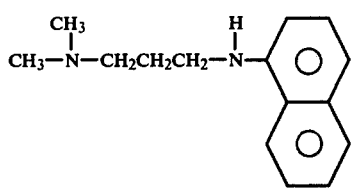

1-dimethylamino-3-(alpha naphthylamino)-propane.

5. The marker for petroluem fuels of claim 1 wherein the marker is the compound

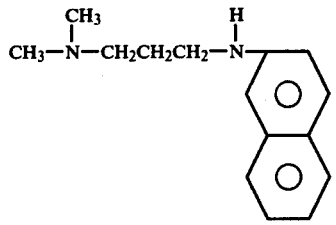

1-diethylamino-3-(beta naphthylamino)-propane.

6. The marker for petroleum fuels of claim 1 wherein the marker is the compound

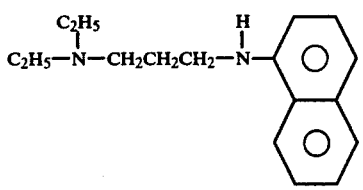

1-diethylamino-3-(alpha naphthylamino)-propane.

7. The marker for petroleum fuels of claim 1 wherein the marker is the compound

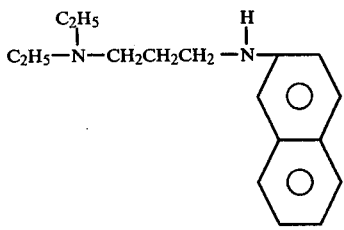

1-diethylamino-3-(beta naphthylamino)-propane.

8. A method of marking a petroleum fuel with a marker, said method comprising dissolving in said fuel at least about 0.5 part per million of a marker selected from the group consisting of:

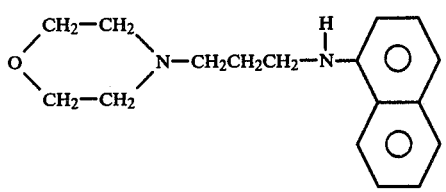

(I)

1-(4-morpholino)-3-(alpha naphthylamino)-propane,

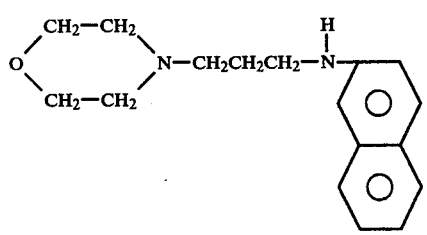

(II)

1-(4-morpholino)-3-(beta naphthylamino)-propane,

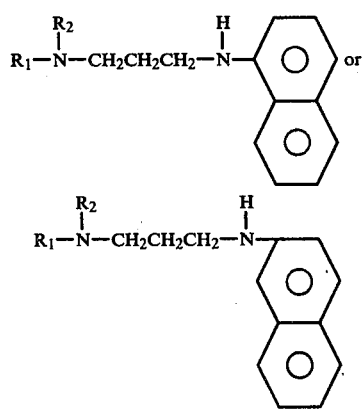

(III)

(IV)

where $R_1$ and $R_2$ may each be hydrogen or alkyl having from one to twenty carbon atoms.

9. The method of claim 8 wherein the marker is 1-(4-morpholino)-3-(alpha naphthylamino)-propane.

10. The method of claim 8 wherein the marker is 1(4-morpholino)-3-(beta naphthylamino)-propane.

11. The method of claim 8 wherein the marker is 1-dimethylamino-3-(alpha naphthylamino)-propane.

12. The method of claim 8 wherein the marker is 1-dimethylamino-3-(beta naphthylamino)-propane.

13. The method of claim 8 wherein the marker is 1-diethylamino-3-(alpha naphthylamino)-propane.

14. The method of claim 8 wherein the marker is 1-diethylamino-3-(beta naphthylamino)-propane.

15. The method of claim 8 wherein the marker is a compound having the formula

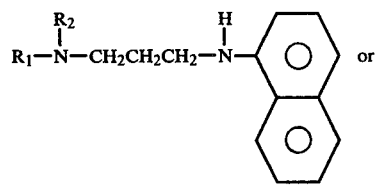

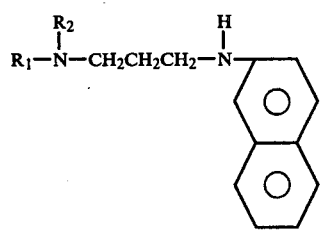

where $R_1$ and $R_2$ may each be hydrogen or alkyl having from 8 to 18 carbon atoms.

16. A method of detecting the presence in a petroleum fuel of at least about 0.5 part per million of a marker selected from the group consisting of

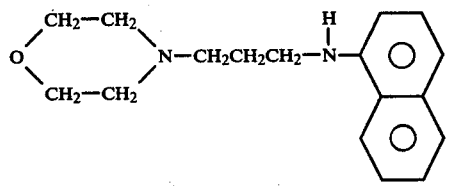

1-(4-morpholino)-3-(alpha naphthylamino)-propane,

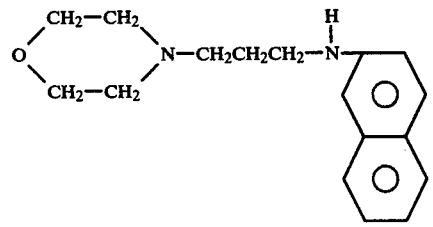

1-(4-morpholino)-3-(beta naphthylamino)-propane,

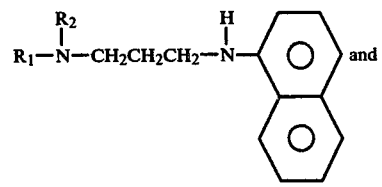

and

-continued

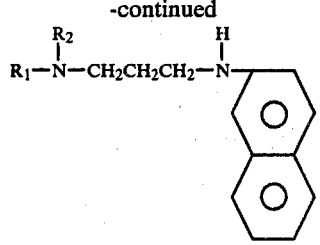

where $R_1$ and $R_2$ may each be hydrogen or alkyl having from one to twenty carbon atoms, said method comprising (I) extracting said marker from said marked fuel with an aqueous acidic extractant and (II) admixing with the aqueous acidic extract so obtained a solution of diazotized 2-chlor-4-nitroaniline whereupon a characteristic coloration is obtained.

17. The method of claim 16 wherein the marker is 1-(4-morpholino)-3-(alpha naphthylamino)-propane.

18. The method of claim 16 wherein the marker is 1-(4-morpholino)-3-(beta naphthylamino)-propane.

19. The method of claim 16 wherein the marker is 1-dimethylamino-3-(alpha naphthylamino)-propane.

20. The method of claim 16 wherein the marker is 1-dimethylamino-3-(beta naphthylamino)-propane.

21. The method of claim 16 wherein the marker is 1-diethylamino-3-(alpha naphthylamino)-propane.

22. The method of claim 16 wherein the marker is 1-diethylamino-3-(beta naphthylamino)-propane.

23. The method of claim 16 wherein the marker is a compound having the formula

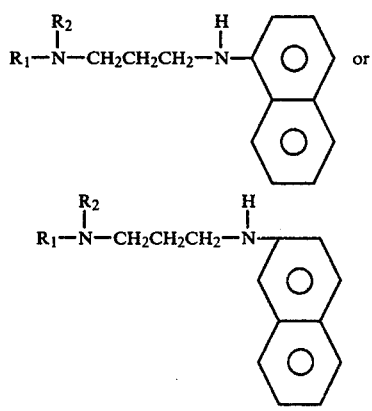

wherein $R_1$ and $R_2$ may each be hydrogen or alkyl having from 1 to 20 carbon atoms.

24. A marked petroleum fuel having dissolved therein at least 0.5 part per million of a marker selected from the group consisting of

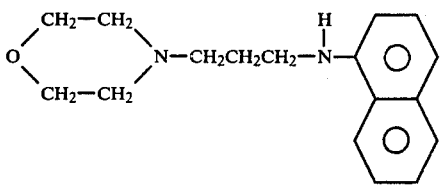

1-(4-morpholino)-3-(alpha naphthylamino)-propane,

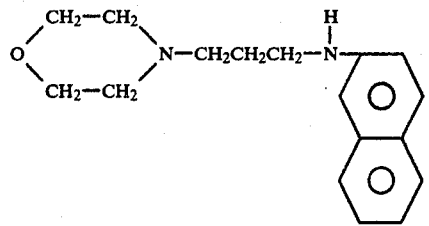

1-(4-morpholino)-3-(beta naphthylamino)-propane,

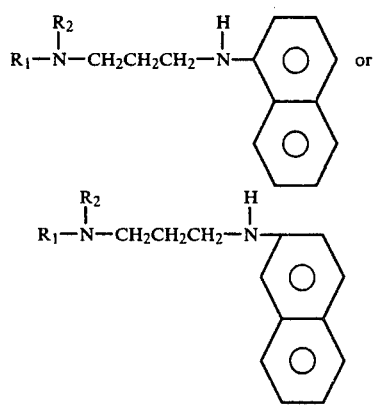

where $R_1$ and $R_2$ may each be hydrogen or alkyl having from one to twenty carbon atoms.

25. The marked petroleum fuel of claim 24 wherein the marker is 1-(4-morpholino)-3-(alpha naphthylamino)-propane.

26. The marked petroleum fuel of claim 24 wherein the marker is 1-(4-morpholino)-3-(beta naphthylamino)-propane.

27. The marked petroleum fuel of claim 24 wherein the marker is 1-dimethylamino-3-(alpha naphthylamino)-propane.

28. The marked petroleum fuel of claim 24 wherein the marker is 1-dimethylamino-3-(beta naphthylamino)-propane.

29. The marked petroleum fuel of claim 24 wherein the marker is 1-dimethylamino-3-(alpha naphthylamino)-propane.

30. The marked petroleum fuel of claim 24 wherein the marker is 1-diethylamino-3-(beta naphthylamino)-propane.

31. The marked petroleum fuel of claim 24 wherein the marker is a compound having the formula where $R_1$ and $R_2$ may each be hydrogen or alkyl having from one to twenty carbon atoms.

* * * * *